United States Patent
Day

(10) Patent No.: US 10,435,654 B2
(45) Date of Patent: Oct. 8, 2019

(54) ANTIMICROBIAL COMPOSITIONS DERIVED FROM HIGH-LAURIC VEGETABLE OILS

(71) Applicant: Burke Pharmaceuticals, Inc., Hot Springs, AR (US)

(72) Inventor: Charles Day, Leitchfield, KY (US)

(73) Assignee: Burke Pharmaceuticals, Inc., Hot Springs, AR (US)

( * ) Notice: Subject to any disclaimer, the term of this patent is extended or adjusted under 35 U.S.C. 154(b) by 0 days.

(21) Appl. No.: 16/294,390

(22) Filed: Mar. 6, 2019

(65) Prior Publication Data

US 2019/0276776 A1 Sep. 12, 2019

Related U.S. Application Data

(60) Provisional application No. 62/639,196, filed on Mar. 6, 2018.

(51) Int. Cl.

| | |
|---|---|
| *C11D 9/02* | (2006.01) |
| *C11D 9/00* | (2006.01) |
| *C11D 9/38* | (2006.01) |
| *A01N 31/02* | (2006.01) |
| *A01N 65/44* | (2009.01) |

(52) U.S. Cl.
CPC .............. *C11D 9/002* (2013.01); *A01N 31/02* (2013.01); *A01N 65/44* (2013.01); *C11D 9/38* (2013.01)

(58) Field of Classification Search
None
See application file for complete search history.

(56) References Cited

PUBLICATIONS

K.A. Hammer, C.F. Carson, and T.V. Riley. 1999. Antimicrobial activity of essential oils and other plant extracts. Journal of Applied Microbiology 86: 985-990.
D.S. Knutzon, T.R. Hayes, A. Wyrick, H. Xiong, H. Maelor Davies, and T.A. Voleker. 1999. Lysophosphatidic acid acyltransferase from coconut endosperm mediates the insertion of laurate at the sn-2 position of triacylglycerols in lauric rapeseed oil and can increase total laurate levels. Plant Physiol. 120: 739-746.
S. Lieberman, M.G. Enig, and H.G. Preuss. 2006. A review of monolaurin and lauric acid: natural virucidal and bactericidal agents. Alternative & Complementary Therapies 12: 310-314.
P. Tangwatcharin and P. Khopaibool. 2012. Activity of virgin coconut oil, lauric acid or monolaurin in combination with lactic acid against *Staphylococcus aureus*. Southeast Asian J. Trop. Med. Public Health 43: 969-985.
T. Nakatsuji, M.C. Kao, J-Y. Fang, C.C. Zouboulis, L. Zhang, R.L. Gallo, and C-M. Huang. 2009. Antimicrobial property of lauric acid against Propionibacterium acnes: Its therapeutic potential for inflammatory acne vulgaris. J. Invest. Dermatol. 129: 2480-2488.
W.C. Huang, T.H. Tsai, L.T. Chuang, Y.Y. Li, C.C. Zouboulis, and P.J. Tsai. 2013. Anti-bacterial and anti-inflammatory properties of capric acid against Propionibacterium acnes: a comparative study with lauric acid. J. Dermatol. Sci. 73: 232-240.

*Primary Examiner* — Necholus Ogden, Jr.
(74) *Attorney, Agent, or Firm* — Husch Blackwell LLP

(57) ABSTRACT

Provided herein are antimicrobial compositions comprising derivatives of lauric acid, and methods for preparing and using such compositions. As a non-limiting example, a process for preparing an antimicrobial composition may comprise: (1) a saponification step wherein a high-lauric vegetable oil is contacted with a strong base, thereby providing a high-laurate soap component; (2) a lipolysis step wherein a high-lauric vegetable oil is contacted with a lipase, thereby providing a lipolyzed oil composition comprising glycerol monolaurate; and (3) a combination step wherein the soap composition is combined with the lipolyzed oil composition, thereby providing the antimicrobial foaming soap composition.

29 Claims, No Drawings

ANTIMICROBIAL COMPOSITIONS DERIVED FROM HIGH-LAURIC VEGETABLE OILS

CROSS-REFERENCE TO RELATED APPLICATIONS

This application claims priority to and the benefit of U.S. Provisional App. Ser. No. 62/639,196 filed Mar. 6, 2018, the entire contents of which are incorporated herein by reference.

BACKGROUND

A strong consumer demand exists for anti-bacterial products, and particularly for anti-bacterial soaps and hand sanitizers. Concerns about the development of drug-resistant bacteria, however, have led to increasingly stringent government regulation of synthetic chemicals that provide antibacterial activity.

As of September 2017, the U.S. Food and Drug Administration (FDA) has prohibited the use of thirteen compounds that had been used for decades to create antibacterial surfactants. The most widely used of these compounds, triclosan, was the active anti-bacterial ingredient in 93% of consumer anti-bacterial soaps. Three additional anti-bacterial chemicals that have commonly been used in consumer products are currently under FDA review, and may also become prohibited for use within the next several years.

Accordingly, there exists an urgent need in the industry to develop products that provide antimicrobial activity in the absence of any anti-bacterial compounds that have been prohibited by the FDA or are currently under FDA review.

SUMMARY

Provided herein is a method for preparing an antimicrobial composition, the method comprising combining a soap composition comprising a high-laurate soap component with a lipolyzed oil composition comprising glycerol monolaurate. Preferably, the high-laurate soap component comprises at least about 5% by weight of a lauric acid salt, and the concentration of glycerol monolaurate in the lipolyzed oil composition is at least about 2 mM.

Also provided herein is a method for preparing an antimicrobial composition, the method comprising a saponification step wherein a high-lauric vegetable oil is contacted with a strong base, thereby providing a high-laurate soap component; a lipolysis step wherein a high-lauric vegetable oil is contacted with a lipase, thereby providing a lipolyzed oil composition comprising glycerol monolaurate; and a combination step wherein the soap composition is combined with the lipolyzed oil composition.

Also provided herein is an antimicrobial composition comprising glycerol monolaurate and a high-laurate soap component. Preferably, the composition comprises glycerol monolaurate in a concentration of at least about 2 mM, and the high-laurate soap component comprises at least about 5% by weight of a lauric acid salt. The antimicrobial composition may be, for example, in the form of a solid, liquid, or gel composition. Non-limiting examples of antimicrobial compositions that may be prepared according to the present disclosure include antimicrobial foaming soap compositions and antimicrobial hand sanitizer compositions.

DETAILED DESCRIPTION

Provided herein are antimicrobial compositions comprising derivatives of lauric acid, and methods for preparing and using such compositions. Advantageously, the compositions described herein provide antimicrobial activity without requiring the addition of any anti-bacterial compounds that have been prohibited by the U.S. Food and Drug Administration.

Laurie acid and the salts and esters thereof (referred to in the art as "laurates") exhibit a broad range of antimicrobial activity, including antibacterial, antifungal, virucidal, and antiprotozoal activity. Non-limiting examples of laurates that exhibit antimicrobial activity include lauric acid, sodium laurate, potassium laurate, and glycerol monolaurate.

As described in detail below, laurate compounds having antimicrobial activity may be obtained by processing a high-lauric vegetable oil according to one or more of the methods provided herein. As used herein, the term "high-lauric vegetable oil" refers to a plant-derived oil having a significant concentration of lauric acid, such that lauric acid accounts for at least about 5% by weight of the total fatty acid content. Preferably, the high-lauric vegetable oil is a vegetable oil wherein lauric acid accounts for at least about 10%, at least about 15%, at least about 20%, at least about 25%, at least about 30%, at least about 35%, at least about 40%, or at least about 45% of the total fatty acid content.

Non-limiting examples of high-lauric vegetable oils include bacuaçu palm oil, babassu oil, cohune oil, murumuru butter, peach palm kernel oil, coconut oil, palm kernel oil, laurel oil, high lauric rapeseed oil (also referred to as high lauric canola oil), and medium chain triglycerides. Examples of preferred high-lauric vegetable oils include coconut oil, palm kernel oil, laurel oil, and high lauric rapeseed oil. For example, lauric acid accounts for approximately 48% of the total fatty acid content in coconut oil, which is particularly preferred for use in the compositions and methods provided herein.

The methods described herein can be used to prepare a wide variety of compositions having antimicrobial activity provided by the presence of laurate compounds. As non-limiting examples, methods for preparing a foaming soap composition and a hand sanitizer composition are described in detail below. Those skilled in the art will appreciate that a wide variety of antimicrobial formulations can be prepared using the same principles, for example by incorporating a lipolyzed oil composition and/or a high-laurate soap component prepared as generally described below.

Preparation of an Antimicrobial Foaming Soap Composition

For example, provided herein are various methods for preparing an antimicrobial foaming soap composition. In one embodiment, the method comprises combining a soap composition comprising a high-laurate soap component with a lipolyzed oil composition comprising glycerol monolaurate.

As described in further detail below, the high-laurate soap component may optionally be prepared via a saponification step in which a high-lauric vegetable oil is contacted with a strong base. As also described below, the lipolyzed oil composition may optionally be prepared via a lipolysis step wherein a high-lauric vegetable oil is contacted with a lipase.

In preferred embodiments, the same high-lauric vegetable oil is used to produce both the high-laurate soap component and the lipolyzed oil composition. For example, in particularly preferred embodiments, the high-laurate soap component and the lipolyzed oil composition are each derived from coconut oil.

Accordingly, as a non-limiting example, a process for preparing an antimicrobial foaming soap composition may comprise: (1) a saponification step wherein a high-lauric vegetable oil is contacted with a strong base, thereby providing a high-laurate soap component; (2) a lipolysis step wherein a high-lauric vegetable oil is contacted with a lipase, thereby providing a lipolyzed oil composition comprising glycerol monolaurate; and (3) a combination step wherein the soap composition is combined with the lipolyzed oil composition, thereby providing the antimicrobial foaming soap composition.

Preparation of the High-Laurate Soap Component

In some embodiments, the method comprises a saponification step wherein a high-lauric vegetable oil is contacted with a strong base, thereby providing a high-laurate soap component.

In a saponification reaction involving a triglyceride and a strong base, the end products of the saponification reaction are fatty acid salts (i.e., soaps) and glycerol. Accordingly, in a saponification reaction involving triglycerides derived from a high-lauric vegetable oil, the end product will include a significant portion of laurate salts.

Strong bases suitable for use in saponification reactions are generally known to those skilled in the art. Preferably, the strong base comprises a sodium or potassium cation, and most preferably a sodium cation. Non-limiting examples of suitable strong bases include sodium hydroxide and potassium hydroxide. A particularly preferred strong base is sodium hydroxide.

Preferably, the high-laurate soap component comprises at least about 5% by weight of a lauric acid salt. For example, the high-laurate soap component can comprise at least about 10% by weight, at least about 15% by weight, at least about 20% by weight, at least about 25% by weight, at least about 30% by weight, at least about 35% by weight, at least about 40% by weight, or at least about 45% by weight of the lauric acid salt.

Non-limiting examples of suitable lauric acid salts include sodium laurate, potassium laurate, and combinations thereof. In preferred embodiments, the lauric acid salt comprises sodium laurate.

Preparation of the Lipolyzed Oil Composition

In some embodiments, the method comprises a lipolysis step wherein a high-lauric vegetable oil is contacted with a lipase.

Generally, upon contact with a triglyceride substrate, a lipase will convert the triglyceride to one monoglyceride and two free fatty acids. For example, if the triglyceride is derived from a high-lauric vegetable oil, the end products of the lipolysis reaction will include lauric acid and glycerol monolaurate.

In a particularly preferred embodiment, the lipase has a specificity for one or more positions on a triglyceride substrate, such that it promotes the production of glycerol monolaurate when contacted with the high-lauric vegetable oil.

For example, when the high-lauric vegetable oil comprises coconut oil, it is preferable to utilize a lipase that has a specificity for the sn-1,3 positions of a triglyceride substrate. In coconut oil triglycerides, the sn-2 position is mostly occupied by laurate. Accordingly, when a lipase with sn-1,3 specificity acts on triglycerides derived from coconut oil, the specificity of the lipase promotes the production of glycerol monolaurate, and the 2-lauryl glycerol isomer in particular.

Non-limiting examples of lipases that have a specificity for the sn-1,3 positions of triglycerides include human pancreatic lipase, bovine pancreatic lipase, porcine pancreatic lipase, and a variety of microbial lipases.

Depending on the how the lipolysis reaction is carried out, the lipase may or may not remain present in the reaction mixture following completion of the reaction. For example, the lipolysis reaction may be carried out using a lipase that is immobilized on a solid support and removed upon completion of the reaction. Accordingly, in some embodiments, the antimicrobial composition does not comprise lipase, or comprises only a residual quantity of lipase.

Alternatively, the lipolysis reaction may be carried out by combining free (i.e., non-immobilized) lipase with the high-lauric vegetable oil. Accordingly, in some embodiments, the antimicrobial composition can comprise lipase.

Optionally, the high-lauric vegetable oil may be diluted in water to form an aqueous emulsion before being contacted with the lipase. Without being bound to a particular theory, it is believed that emulsifying the high-lauric vegetable oil in water increases the total surface area of the oil that is available to the lipase, and therefore increases the rate of the lipolysis reaction.

Following the lipolysis step, the lipolyzed oil composition may optionally be contacted with a strong base to neutralize at least a portion of the free fatty acids liberated by the lipase. The strong base may be selected as generally described above. For example, the strong base may comprise sodium hydroxide. In preferred embodiments, the lipolyzed oil composition is contacted with a strong base in an amount sufficient to neutralize substantially all of the free fatty acids liberated by the lipase.

The concentration of glycerol monolaurate in the lipolyzed oil composition is preferably at least about 2 mM, for example, at least about 3 mM, at least about 4 mM, at least about 5 mM, at least about 7.5 mM, at least about 10 mM, at least about 12.5 mM, at least about 15 mM, at least about 17.5 mM, at least about 20 mM, or at least about 25 mM.

Advantageously, and without being bound to a particular theory, it is currently believed that 2-lauryl glycerol exhibits superior antimicrobial activity relative to 1-lauryl glycerol, which is the more common isomer of glycerol monolaurate. In preferred embodiments, the glycerol monolaurate in the lipolyzed oil composition is predominately in the form of the 2-lauryl glycerol isomer. For example, 2-lauryl glycerol may comprise at least about 50% by weight, at least about 60% by weight, at least about 70% by weight, at least about 80% by weight, at least about 90% by weight, or at least about 95% by weight of the total amount of glycerol monolaurate in the composition. The concentration of 2-lauryl glycerol may be, for example, at least about 2 mM, for example, at least about 3 mM, at least about 4 mM, at least about 5 mM, at least about 7.5 mM, at least about 10 mM, at least about 12.5 mM, at least about 15 mM, at least about 17.5 mM, at least about 20 mM, or at least about 25 mM.

Preparation of a Hand Sanitizer Composition

Also provided herein are various methods for preparing a hand sanitizer composition comprising one or more derivatives of lauric acid. In one embodiment, the method comprises combining a soap composition comprising a high-laurate soap component, a lipolyzed oil composition comprising glycerol monolaurate, a thickener, and an alcohol.

A soap composition comprising a high-laurate soap component may optionally be prepared via a saponification step in which a high-lauric vegetable oil is contacted with a strong base, as described in detail above. Likewise, the lipolyzed oil composition may optionally be prepared via a lipolysis step wherein a high-lauric vegetable oil is contacted with a lipase, as described in detail above.

Accordingly, as a non-limiting example, a process for preparing the hand sanitizer composition may comprise: (1) a saponification step wherein a high-lauric vegetable oil is contacted with a strong base, thereby providing a high-laurate soap component; (2) a lipolysis step wherein a high-lauric vegetable oil is contacted with a lipase, thereby providing a lipolyzed oil composition comprising glycerol monolaurate; and (3) a combination step wherein the soap composition is combined with the lipolyzed oil composition, a thickener, and an alcohol, thereby providing the hand sanitizer composition.

Thickener

The hand sanitizer composition may further comprise a thickener. The thickener may be useful, for example, to modify the rheological properties of the composition (such as density and/or viscosity) as desired for a particular hand sanitizer formulation.

Suitable thickeners include polymers such as polyethylene glycol, polyacrylic acid, and derivatives thereof. A non-limiting example of a suitable thickener is a polyvinyl carboxy polymer crosslinked with ethers of pentaerythritol, commercially available from Lubrizol Advanced Materials, Inc. under the name Carbomer 980 QD.

Alcohol

The hand sanitizer composition may further comprise an alcohol. In addition to providing germicidal activity, alcohols are advantageous in hand sanitizer compositions because they dry quickly and leave behind little or no residue on the user's hands.

Non-limiting examples of alcohols that can be incorporated into the hand sanitizer composition include ethanol and isopropanol.

Antimicrobial Compositions

Also provided herein are antimicrobial compositions comprising one or more derivatives of lauric acid. The antimicrobial composition may be in the form of a liquid, a gel, a solid bar, or any other form suitable for application to the skin. As non-limiting examples, the antimicrobial composition may be a soap bar (i.e., a solid) or a hand sanitizer composition (i.e., a liquid or gel).

Generally, the antimicrobial compositions provided herein may be prepared by any methods known to those skilled in the art. In preferred embodiments, the antimicrobial compositions may be prepared according to the methods described above. Non-limiting examples of specific formulations that may be prepared according to the present disclosure include antimicrobial soap compositions and hand sanitizer compositions.

For example, provided herein is an antimicrobial composition comprising a high-laurate soap component, glycerol monolaurate, and water. The antimicrobial composition may optionally be prepared according to a method as described in detail above.

The antimicrobial composition preferably comprises the high-laurate soap component in an amount of from about 1% to about 25% by weight, relative to the composition as a whole. For example, the antimicrobial foaming soap composition can comprise the high-laurate soap component in an amount of from about 1% to about 20% by weight, from about 2% to about 10% by weight, or from about 2% to about 8% by weight relative to the composition as a whole.

The high-laurate soap component preferably comprises at least about 5% by weight of a lauric acid salt, relative to the composition as a whole. For example, the high-laurate soap component can comprise at least about 10% by weight, at least about 15% by weight, at least about 20% by weight, at least about 25% by weight, at least about 30% by weight, at least about 35% by weight, at least about 40% by weight, or at least about 45% by weight of the lauric acid salt relative to the composition as a whole. Suitable lauric acid salts may be selected as described in detail above.

The antimicrobial composition preferably comprises the lauric acid salt in a concentration of at least about 50 mM, for example, at least about 60 mM, at least about 70 mM, at least about 80 mM, at least about 90 mM, or at least about 100 mM.

The antimicrobial composition preferably comprises glycerol monolaurate in a concentration of at least about 0.05 mM, for example, at least about 0.1 mM, at least about 0.2 mM, at least about 0.3 mM, at least about 0.4 mM, at least about 0.5 mM, or at least about 1 mM. More typically, the antimicrobial composition comprises glycerol monolaurate in a concentration of at least about at least about 2 mM, for example, at least about 3 mM, at least about 4 mM, at least about 5 mM, at least about 7.5 mM, at least about 10 mM, at least about 12.5 mM, at least about 15 mM, at least about 17.5 mM, at least about 20 mM, or at least about 25 mM. In some embodiments, the concentration of glycerol monolaurate may range from about 0.05 mM to about 50 mM, for example from about 5 mM to about 50 mM, from about 10 mM to about 30 mM, or from about 10 mM to about 25 mM.

In preferred embodiments, the glycerol monolaurate is predominately in the form of the 2-lauryl glycerol isomer. For example, 2-lauryl glycerol may comprise at least about 50% by weight, at least about 60% by weight, at least about 70% by weight, at least about 80% by weight, at least about 90% by weight, or at least about 95% by weight of the total amount of glycerol monolaurate in the composition. For example, the antimicrobial composition may comprise 2-lauryl glycerol in a concentration of at least about 2 mM, for example, at least about 3 mM, at least about 4 mM, at least about 5 mM, at least about 7.5 mM, at least about 10 mM, at least about 12.5 mM, at least about 15 mM, at least about 17.5 mM, at least about 20 mM, or at least about 25 mM. In some embodiments, the concentration of 2-lauryl glycerol may range from about 0.05 mM to about 50 mM, for example from about 5 mM to about 50 mM, from about 10 mM to about 30 mM, or from about 10 mM to about 25 mM.

The antimicrobial compositions described herein may each contain water. Those skilled in the art will understand that the amount of water added to a given composition will vary based on the relative concentrations of other components, the presence or absence of other solvents, and the intended use of the composition, among other factors.

In some embodiments, for example when the composition is an antimicrobial foaming soap formulation, the composition comprises water in a concentration of at least about 50% by weight, for example at least about 60% by weight, at least about 70% by weight, at least about 80% by weight, or at least about 90% by weight relative to the composition as a whole. For example, the composition may comprise water in a concentration of from about 60% to about 99% by weight, for example from about 80% to about 98% by weight, from about 85% to about 97% by weight, or from about 88% to about 95% by weight relative to the composition as a whole.

In some embodiments, for example when the composition is a hand sanitizer formulation, the composition comprises an alcohol in an amount of from about 20% by volume to about 80% by volume, relative to the composition as a whole. For example, the alcohol concentration may range from about 25% by volume to about 60% by volume, from about 25% by volume to about 55% by volume, or from about 30% by volume to about 50% by volume, relative to the composition as a whole. The alcohol may be selected as generally described above.

The antimicrobial composition may optionally comprise a thickener, which may be selected as described above. The antimicrobial composition preferably comprises the thickener in a concentration of at least about 2 mg/ml, for example, at least about 3 mg/ml, at least about 4 mg/ml, or at least about 5 mg/ml relative to the composition as a whole. For example, the antimicrobial composition may comprise a thickener in an amount of from about 2 mg/ml to about 20 mg/ml, from about 4 mg/ml to about 20 mg/ml, or from about 5 mg/ml to about 15 mg/ml.

The antimicrobial composition may further comprise one or more essential oils. Essential oils may be selected to provide the antimicrobial composition with a pleasing aroma, or other desirable cosmetic properties. In preferred embodiments, the antimicrobial composition comprises an essential oil having antimicrobial activity. A non-limiting example of an essential oil having antimicrobial activity is lemongrass oil. An essential oil may be present, for example, in an amount of at least about 0.2% by volume relative to the composition as a whole. In preferred embodiments, the concentration of the essential oil is from about 0.2% by volume to about 20% by volume, relative to the composition as a whole, for example from about 0.5% by volume to about 10% by volume, or from about 1% by volume to about 5% by volume relative to the composition as a whole.

In some embodiments, the antimicrobial composition may comprise a lipase. When a lipase is present, the concentration of lipase typically ranges from about 0.01% to about 0.5% by weight, for example from about 0.01% to about 0.2% by weight, or from about 0.01% to about 0.1% by weight relative to the composition as a whole.

Those skilled in the art will understand that the antimicrobial composition may further comprise additional components, including but not limited to surfactants, stabilizers, preservatives, dyes, and perfumes, without departing from the scope of the present disclosure.

Other objects and features will be in part apparent and in part pointed out hereinafter.

EXAMPLES

The following non-limiting examples are provided to further illustrate the present disclosure.

Example 1: Components

The components described below were used in each of the following examples, unless otherwise indicated.

Organic virgin coconut oil (coconut oil) was obtained from Sam's Club. Phenolphthalein powder, ACS Reagent Grade, was obtained from Biopharm, Inc., Hatfield, Ark. Sodium chloride and sodium hydroxide were each obtained from Sigma-Aldrich. Hog pancreas lipase, Type II, 100-400 units/mg protein (lipase) was also obtained from Sigma-Aldrich.

Example 2: Preparation of Coconut Oil Soap

In a 250 ml glass beaker, 22.8 g of sodium hydroxide was added to 46 g of distilled water, stirred until dissolved and poured into a crock pot on low heat. In a separate 250 ml beaker, 127.2 g of coconut oil was weighed and then poured into the sodium hydroxide solution within the heated crock pot. The solution was immediately stirred for 2-3 minutes with an immersion blender until it reached trace. After 30 minutes, the hot soap was scooped into bar soap molds to cool overnight at room temperature.

Example 3: Preparation of Coconut Oil Emulsion

In order to make the oil and water emulsion, 500 mg of the coconut oil soap, prepared as described in Example 2, was added to 10 ml distilled water in a 120 ml glass screw cap reaction jar and dissolved by stirring. In the 120 ml glass screw cap, 63.6 g of coconut oil was then added, the screw cap secured, and the contents mixed by vigorous shaking until a thick milky white emulsion formed.

Example 4: Lipase Reaction

Disposable 2-ounce plastic mini-cups (plastic cup) with lids were purchased from Diamond Daily, Hearthmark LLC, Fishers, Ind. Into the plastic cup was pipetted 1.0 ml of coconut oil emulsion, prepared as described in Example 3, followed by 8.0 ml of 0.9% sodium chloride, and the contents were then mixed by gentle swirling. Next, 1.0 ml of 2.0% pancreatic lipase solution in 0.9% sodium chloride was added to the plastic cup, and mixed by swirling. The plastic cup was then capped and placed in a 40° C. incubator for approximately 5 days. After incubation, the lid was removed from the cup, and one drop of a 1.0% solution of phenolphthalein dissolved in 50% ethanol/water was added to the cup. The contents in the cup were then titrated to a pink endpoint with 25 ml of 0.1N sodium hydroxide to provide a final lipolyzed oil composition with a volume of 35 ml. The control used 1.0 ml of 0.9% sodium chloride, rather than the 2% lipase solution.

Example 5: Preparation of Antimicrobial Foaming Soap Formulation

In order to convert the lipase reactions to their sodium salts, 25 ml of 0.10 N sodium hydroxide was added to the solution within the cup, prepared as described in Example 4, and mixed. Next, 1750 mg of coconut oil soap, prepared as described in Example 1, was dissolved in the 35 ml lipolyzed oil composition to create the foaming soap formulation.

Example 6: Preparation of Solutions for a Hand Sanitizer

Three solutions for the preparation of the hand sanitizer were made. For the first solution, coconut oil soap, prepared as described in Example 1, was made. 600 mg of the coconut oil soap flakes was dissolved in 10 ml of distilled water.

Coconut oil soap, prepared as described in Example 2, and coconut oil emulsion, prepared as described in Example 3, were used to prepare the second solution. First, 1.0 ml of coconut oil emulsion was diluted with 8.0 ml of 0.9% sodium chloride. The resulting emulsion was added to 0.1 ml of 2% lipase, followed by incubation at 40° C. for approximately 5 days. After incubation, 25 ml of 0.1 N sodium hydroxide was added and mixed to the emulsion to create a lipolyzed coconut oil solution. The second solution was 10 ml of lipolyzed coconut oil.

The third solution was made by adding 2 drops of 0.1 N hydrogen chloride to 10 ml of distilled water. 400 mg of Carbomer 980 QD, purchased from MakingCosmetics.com, was slowly sprinkled onto the 10 ml of distilled water and hydrogen chloride and dissolved.

Example 7: Preparation of Hand Sanitizer Formulation

In order to prepare the hand sanitizer, the first solution and second solution, prepared as described in Example 6, were mixed and then poured into the third solution, also prepared as described in Example 6. The resulting combination was mixed with a metal spatula until a stiff white paste was formed.

Four 5 ml aliquots of 95% ethanol were created. One 5 ml aliquot of 95% ethanol was added, at a time, to the resulting combination and mixed each time to create a smooth consistency. After the fourth aliquot of 95% ethanol was added and mixed, the resulting combination had a smooth pudding-like consistency. 1.0 ml of *Cymbopogon citratus* (lemongrass oil) essential oil may be added to the combination and mixed, until the combination again had a smooth pudding-like consistency.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

In view of the above, it will be seen that several objects of the disclosure are achieved and other advantageous results attained.

As various changes could be made in the above products and methods without departing from the scope of the disclosure, it is intended that all matter contained in the above description shall be interpreted as illustrative and not in a limiting sense.

What is claimed is:

1. An antimicrobial composition comprising:
at least about 50% by weight of 2-lauryl glycerol;
and a high-laurate soap component,
wherein the composition comprises 2-lauryl glycerol in a concentration of at least about 2 mM;
and wherein the high-laurate soap component comprises at least about 5% by weight of a lauric acid salt.

2. The composition of claim 1 wherein the soap component comprises the lauric acid salt in a concentration of at least about 10% by weight.

3. The composition of claim 1 wherein the lauric acid salt is selected from the group consisting of sodium laurate, potassium laurate, and combinations thereof.

4. The composition of claim 3 wherein the lauric acid salt comprises sodium laurate.

5. The composition of claim 1 comprising 2-lauryl glycerol in a concentration of at least about 5 mM.

6. The composition of claim 1 comprising glycerol monolaurate in a concentration of from about 5 mM to about 50 mM.

7. The composition of claim 1 wherein at least about 80% by weight of the glycerol monolaurate is 2-lauryl glycerol.

8. The composition of claim 7 wherein at least about 95% by weight of the glycerol monolaurate is 2-lauryl glycerol.

9. The composition of claim 1 comprising the high-laurate soap component in a concentration from about 1% by weight to about 25% by weight, relative to the composition as a whole.

10. The composition of claim 9 further comprising water in a concentration of at least about 50% by weight, relative to the composition as a whole.

11. The composition of claim 9 further comprising an alcohol in a concentration of from about 20% by volume to about 80% by volume, relative to the composition as a whole.

12. The composition of claim 11 further comprising a thickener in a concentration of from about 2 mg/ml to about 20 mg/ml.

13. The composition of claim 11 further comprising an essential oil.

14. The composition of claim 13 wherein the essential oil exhibits antimicrobial activity.

15. The composition of claim 14 wherein the essential oil comprises lemongrass oil.

16. A method for preparing an antimicrobial composition according to claim 1, the method comprising:
combining a soap composition comprising a high-laurate soap component with a lipolyzed oil composition comprising at least 50% of a 2-lauryl glycerol,
wherein the high-laurate soap component comprises at least about 5% by weight of a lauric acid salt,
and the concentration of 2-lauryl glycerol in the lipolyzed oil composition is at least about 2 mM.

17. The method of claim 16 wherein the high-laurate soap component is prepared via a saponification step in which a high-lauric vegetable oil is contacted with a strong base.

18. The method of claim 17 wherein the lipolyzed oil composition is prepared via a lipolysis step wherein a high-lauric vegetable oil is contacted with a lipase.

19. The method of claim 18 wherein the lipase has a specificity for the sn-1,3 positions of a triglyceride substrate.

20. The method of claim 19 wherein the high-lauric vegetable oil used in the lipolysis step comprises coconut oil.

21. The method of claim 18 wherein the same high-lauric vegetable oil is used in both the saponification step and the lipolysis step.

22. The method of claim 21 wherein the high-lauric vegetable oil comprises coconut oil.

23. The method of claim 18 wherein following the lipolysis step, the lipolyzed oil composition is contacted with a strong base to neutralize at least a portion of the free fatty acids liberated by the lipase.

24. The method of claim 18 wherein the high-laurate soap component comprises the lauric acid salt in a concentration of at least about 10% by weight.

25. The method of claim 24 wherein the lauric acid salt is selected from the group consisting of sodium laurate, potassium laurate, and combinations thereof.

26. The method of claim 18 wherein the lipolyzed oil composition comprises glycerol monolaurate in a concentration of at least about 5 mM.

27. The method of claim 26 wherein at least about 80% by weight of the glycerol monolaurate is 2-lauryl glycerol.

28. The method of claim 27 wherein at least about 95% by weight of the glycerol monolaurate is 2-lauryl glycerol.

29. A method for preparing an antimicrobial composition according to claim 1, the method comprising:
- a saponification step wherein a high-lauric vegetable oil is contacted with a strong base, thereby providing at least 5% by weight of a high-laurate soap component;
- a lipolysis step wherein a high-lauric vegetable oil is contacted with a lipase, thereby providing a lipolyzed oil composition comprising at least about 50% of 2-lauryl glycerol monolaurate; and
- a combination step wherein the soap composition is combined with the lipolyzed oil composition.

* * * * *